United States Patent
Braeken et al.

(10) Patent No.: US 11,668,697 B2
(45) Date of Patent: Jun. 6, 2023

(54) DEVICE FOR ANALYSIS OF CELLS AND A METHOD FOR MANUFACTURING OF A DEVICE

(71) Applicants: IMEC VZW, Leuven (BE); Katholieke Universiteit Leuven, KU LEUVEN R&D, Leuven (BE)

(72) Inventors: Dries Braeken, Leuven (BE); Veerle Reumers, Leuven (BE); Alexandru Andrei, Leuven (BE); Andrea Firrincieli, Leuven (BE); Thomas Pauwelyn, Leuven (BE)

(73) Assignees: IMEC VZW, Leuven (BE); KATHOLIEKE UNIVERSITEIT LEUVEN, KU LEUVEN R&D, Leuven (BE)

( * ) Notice: Subject to any disclaimer, the term of this patent is extended or adjusted under 35 U.S.C. 154(b) by 174 days.

(21) Appl. No.: 16/450,985

(22) Filed: Jun. 24, 2019

(65) Prior Publication Data
US 2019/0391127 A1    Dec. 26, 2019

(30) Foreign Application Priority Data
Jun. 25, 2018 (EP) .................................. 18179541

(51) Int. Cl.
*G01N 33/483* (2006.01)
*C12M 1/42* (2006.01)
*C12M 1/34* (2006.01)

(52) U.S. Cl.
CPC ......... *G01N 33/4836* (2013.01); *C12M 35/02* (2013.01); *C12M 41/46* (2013.01)

(58) Field of Classification Search
USPC ....................................................... 435/287.1
See application file for complete search history.

(56) References Cited

U.S. PATENT DOCUMENTS 5,563,067 A * 10/1996 Sugihara ............ G01N 33/4836
324/692
2007/0020923 A1    1/2007 Kraus et al.
(Continued)

FOREIGN PATENT DOCUMENTS

DE    10254158 A1 *  6/2004  ........... G01N 27/414
EP     1278064 A1 *  1/2003  ......... G01N 33/4836
(Continued)

OTHER PUBLICATIONS

Yong Ju Lee. "Low-impurity, highly conformal atomic layer deposition of titanium nitride using NH3—Ar—H2 plasma treatment for capacitor electrodes". Materials Letters, vol. 59, Issue 6, 2005, pp. 615-617, https://doi.org/10.1016/j.matlet.2004.09.030 (Year: 2004).*

(Continued)

*Primary Examiner* — Donald R Spamer
*Assistant Examiner* — Nathan G Esperon
(74) *Attorney, Agent, or Firm* — Moser Taboada (57) ABSTRACT

A device for analysis of cells comprises: an integrated circuit arrangement on a substrate; a dielectric layer formed above the integrated circuit arrangement; a microelectrode array layer formed above the dielectric layer, said microelectrode array layer comprising a plurality of individual electrodes, wherein each electrode is connected to the integrated circuit arrangement through a via in the dielectric layer; and wherein a plurality of longitudinal trenches in the dielectric layer and the microelectrode array layer are for stimulating cell growth on a surface of the device

15 Claims, 5 Drawing Sheets

(56) References Cited

U.S. PATENT DOCUMENTS

| | | | |
|---|---|---|---|
| 2009/0322309 A1* | 12/2009 | Zhu | G01N 33/4836 |
| | | | 174/260 |
| 2011/0269172 A1* | 11/2011 | Eberle | G01N 33/5438 |
| | | | 29/829 |
| 2012/0221256 A1 | 8/2012 | Heal et al. | |
| 2013/0137132 A1* | 5/2013 | Dekker | D06F 75/22 |
| | | | 216/17 |
| 2016/0017268 A1 | 1/2016 | Kim et al. | |
| 2016/0090586 A1* | 3/2016 | Kim | C12N 13/00 |
| | | | 435/283.1 |
| 2020/0173978 A1* | 6/2020 | Hayashi | G01N 33/4836 |

FOREIGN PATENT DOCUMENTS

| | | | | |
|---|---|---|---|---|
| EP | 1965210 A1 | 9/2008 | | |
| WO | WO-00/29637 A1 | 5/2000 | | |
| WO | WO-2014/144219 A1 | 9/2014 | | |
| WO | WO-2014144219 A1 * | 9/2014 | | C12M 23/12 |

OTHER PUBLICATIONS

Graham et al., Commercialisation of CMOS integrated Circuit Technology in Multi-Electrode Arrays for Neuroscience and cell-Based Biosensors, Sensors, vol. 11 No. 5, Mar. 17, 2011, pp. 4943-4971.

Lopez et al., "A 16384-electorde 1024 channel multimodal CMOS MEA for high-throughput intracellular action potential measurements and impedance spectroscopy in drug-screening applications", 2018 IEEE International Solid-State Ciruits Conference—(ISSCC), Feb. 14, 2018 pp. 464-466.

* cited by examiner

DEVICE FOR ANALYSIS OF CELLS AND A METHOD FOR MANUFACTURING OF A DEVICE

The present application claims foreign priority, according to 35 U.S.C. § 119(b), to EP18179541.0 filed Jun. 25, 2018.

TECHNICAL FIELD

The present inventive concept relates to a device for analysis of cells and a method for manufacturing of such a device. In particular, the present inventive concept relates to a device wherein cells are cultured in vitro on a surface of the device.

BACKGROUND

Studying of cell behavior may be of interest in many cell-physiological and medical applications. In order to study cell behavior, cells are typically cultured in vitro.

It is desired that an artificial in vitro environment should stimulate cells to grow and develop in a manner mimicking or corresponding to in vivo cells. The in vitro environment may be shaped by properties of a surface to which cells are attaching.

Microstructures in the surface may induce specific cell growth. This could be due to the microstructures triggering inherent cellular processes which are also found in vivo. For instance, grooves in the surface may be used for aligning cells. Such grooves may thus be used for stimulating cardiac cell cultures to mimic the in vivo structure of a heart.

It is further desired that sensing be performed on the cultured cells so as to allow determining characteristics of the cultured cells. Sensing may be performed indirectly using indirect techniques, e.g. by using label substances to which the cells attach in combination with imaging of the labels.

It would also be of interest to perform electrical sensing in order to detect electrical signals in the cells, especially in electroconductive cells. However, it is challenging to perform electrical sensing on local cells formed on a surface with microstructures.

US 2016/0017268 discloses devices and method comprising microelectrode arrays for differentiation, maturation and functional analysis of electroconductive cells, including muscle cells and neuronal cells. The microelectrode present on the arrays can be used to stimulate and record from cells cultured on a substrate. The substrate may be nanotextured, including an array of substantially parallel grooves and ridges of nanometer-micrometer widths. However, the signals sensed need to be provided to a data acquisition device for processing the signals. In a multi-well embodiment with a large number of parallel wires for providing signals to the data acquisition device, there is a risk of noise, e.g. due to cross talk between wires. Thus, there is still a need for improvement of a device for more robust collection of electrical signals from cells with a high density arrangement of collection of the electrical signals.

SUMMARY

An objective of the present inventive concept is to enable improved analysis of cells and, in particular, for sensing of electrical signals of cells in a dense arrangement of sensing electrodes.

This and other objectives of the present inventive concept are at least partly met by the invention as defined in the independent claims. Preferred embodiments are set out in the dependent claims.

According to a first aspect, there is provided a device for analysis of cells, said device comprising: an integrated circuit arrangement on a substrate; a dielectric layer formed above the integrated circuit arrangement; a microelectrode array layer formed above the dielectric layer, said microelectrode array layer comprising a plurality of individual electrodes, wherein each electrode is connected to the integrated circuit arrangement through a via in the dielectric layer; and a plurality of longitudinal trenches in the dielectric layer and the microelectrode array layer for stimulating cell growth on a surface of the device.

The device according to the first aspect provides a surface on which cell growth is stimulated, in the plurality of longitudinal trenches, such that culturing of cells in an in vitro environment may mimic in vivo behavior. Further, the device enables sensing, possibly in combination with stimulating, of electrical signals of the cells, wherein the sensing may be achieved using electrodes, which may be locally arranged and which may allow a dense arrangement for sensing signals from a plurality of cells.

Thanks to the microelectrode array layer being formed above an integrated circuit arrangement and the electrodes being connected to the integrated circuit arrangement, the signals acquired by electrodes may be locally processed, such as amplified and multiplexed. This implies that signals may be pre-processed and may be selectively provided to be read out from the integrated circuit arrangement. Thus, it may be ensured that signals on adjacent wires connected to the integrated circuit arrangement may not affect each other and that a robust collection of electrical signals in cells may be achieved.

Also, the electrodes being locally connected to an integrated circuit arrangement implies that it may be possible to control how signals are acquired and dynamically change settings of acquiring electrical signals.

The arrangement of the microelectrode array layer above the integrated circuit arrangement also implies that a relatively small footprint of the device may be provided and that the device is compact.

The device comprises a plurality of longitudinal trenches in the dielectric layer and the microelectrode layer. This implies that the trenches may be formed after the microelectrode layer has been formed. This may ensure that deposition of electrode material of the microelectrode array layer need not be controlled for avoiding filling of the trenches and, hence, the forming of the microelectrode layer and the trenches may be achieved with relatively simple steps. Further, the vias may be formed before forming of the trenches so as to allow the electrodes to be connected to the integrated circuit arrangement through the vias.

The dielectric layer may ensure that electrodes are separated from the integrated circuit arrangement except for the connections through the vias. The dielectric layer may be thicker than a depth of the plurality of trenches so as to ensure that the trenches are formed in the dielectric layer and to separate cells growing in the trenches from the integrated circuit arrangement below the dielectric layer.

The dielectric layer, the microelectrode array layer and the plurality of trenches may be formed through back end of line (BEOL) processing after the BEOL processing has formed connections to components (transistors, etc.) on the substrate and interconnected the components with wiring on the substrate. Thus, the dielectric layer may be arranged on a top metal layer of interconnecting layers of the BEOL processing of the device. The electrodes of the microelectrode layer may be connected through the via to the top metal layer of the BEOL processing and, hence, to the components of the integrated circuit arrangement.

By forming the dielectric layer, the microelectrode layer and the trenches in BEOL processing, the manufacturing of the device may be simple and there may be no need of protecting the device after BEOL processing before the dielectric layer, the microelectrode layer and the trenches are formed (in a separate processing procedure).

The cells to be analyzed may be any mammalian cells or mammalian-derived cells, such as human cells or human-derived cells. In particular, it may be of interest to analyze electroconductive cells, such as muscle cells (e.g. cardiomyocytes, skeletal muscle myocytes and smooth muscle myocytes) and neuronal cells. However, the device may also be used with non-electrogenic cells. For instance, the device may be used for measuring a bioimpedance of cells, such as to perform impedance spectroscopy analysis, wherein an impedance is measured for different frequencies of a stimulation signal.

In the context of this application, a layer being arranged "on" or "above" another layer should not be construed as the layers being arranged in a certain relationship with respect to an external reference (such as the earth). Rather, the term should be construed to define an internal relationship between the layers within the structure of the device, which may for instance be related to an order in which the layers are formed on any surface of a substrate (top, bottom or side surfaces). Thus, if the device is arranged so that the layers form a vertical stack, a layer being "on" or "above" another layer indicates that the layer is an upper layer in the stack. Further, it should be realized that a layer being arranged "above" another layer need not be arranged directly on the layer. Rather, there may be one or more intermediate layers in-between.

According to an embodiment, an individual electrode in the microelectrode array layer forms an electrode area, wherein electrode material in the electrode area forms a coherent structure.

By the electrode material forming a coherent structure, all parts of electrode material within the electrode area are in direct contact through the electrode material. This implies that the electrode may be sensitive for acquiring a signal within the electrode area and may be arranged to transfer a signal acquired by any part of the coherent structure to the integrated circuit arrangement. The coherent structure thus ensures that the electrode may be arranged to have a relatively large size for improving acquiring of signals from cells.

According to an embodiment, the via for connecting the electrode to the integrated circuit arrangement is formed in the electrode area.

This implies that the electrode area, in which the electrode is sensitive, may be arranged around the via. Thus, a good coupling of a signal from the electrode to the integrated circuit arrangement may be achieved. Also, a size of an electrode arrangement in the microelectrode array layer may be relatively small, as the via is arranged within the electrode area, which allows arranging adjacent electrodes close to each other such that the device may be provided with a dense arrangement of electrodes.

According to an embodiment, two vias for connecting the electrode to the integrated circuit arrangement are formed in the electrode area.

The use of two vias connecting the electrode to the integrated circuit arrangement may ensure a higher yield in manufacturing of devices, as a redundancy in connection between the electrode and the integrated circuit arrangement is introduced.

Further, the one or more vias may be aligned with longitudinal trench(es) extending in the dielectric layer, such that the one or more vias may extend in the same direction as the longitudinal trenches within the electrode area. The one or more vias may thus improve stimulation of cell growth on the surface of the device. A plurality of vias (such as two or more) may thus be aligned with parallel trenches of the device and the number of vias may be selected based on the vias being aligned with the trenches.

According to an embodiment, a longitudinal trench of the plurality of longitudinal trenches is arranged to extend into the electrode area.

Electrode material on opposite sides of a trench may be connected so as to form a coherent structure in a large area. The connection between the electrode materials on opposite sides of the trench may thus interrupt the longitudinally extending trench.

The longitudinal trenches may define structures stimulating cell growth. By allowing a trench to extending into the electrode area, the trench may be uninterrupted over a large distance. This implies that the arrangement of the electrode may have a small impact on the growth of cells while allowing the coherent structure to be formed in a relatively large area.

According to an embodiment, a groove extending in a common direction with a longitudinal trench of the plurality of longitudinal trenches is arranged within the electrode area.

The groove may contribute to the stimulation of cell growth along the longitudinal trench with which the groove extends in a common direction. This implies that the electrode area is arranged in order to be relatively large, while having small impact on cell growth along longitudinal trenches of the device.

Electrode material on opposite sides of the groove along ridges parallel with the groove may be connected so as to form a coherent structure in a large area. Connections between the electrode materials may be formed at each end of the groove, which implies that two connections may be formed between the electrode material on parallel ridges, which may ensure that the electrode material could be formed as a coherent structure with a high yield.

According to an embodiment, a longitudinal trench of the plurality of longitudinal trenches extends across an entire area of the microelectrode array layer.

When longitudinal trenches extending along a long distance, desired cell growth may be stimulated and achieved. Thus, having at least some longitudinal trenches extend across an entire area of the microelectrode array may ensure that a strong stimulation of desired cell growth is provided.

It should be realized that the longitudinal trenches may, for other reasons, be limited to a particular region of the surface of the device. For instance, part of the area of the microelectrode array layer may be dedicated to other functionality than sensing signals from cells. Thus, the longitudinal trenches need not necessarily extend across an entire area of the microelectrode array.

In another embodiment, a longitudinal trench of the plurality of longitudinal trenches may extend across a distance corresponding to a size of a plurality of electrode areas in microelectrode array.

Thus, the longitudinal trench may extend past a plurality of electrode areas. For instance, the longitudinal trench may extend between two rows of electrode areas, such that the far-extending longitudinal trench may contribute to ensuring that desired cell growth is stimulated.

According to an embodiment, ridges are formed between the plurality of longitudinal trenches and electrode material of the microelectrode array layer is formed on all ridges, wherein the device further comprises stop areas extending perpendicular to the longitudinal trenches, wherein no electrode material is arranged in the stop areas so as to isolate individual electrodes from each other.

The electrode material of the microelectrode array layer may be arranged over a large surface except for in a few stop areas. This implies that the microelectrode array layer may be easily formed without any need of forming complex or small structures in the microelectrode array layer. Then, the plurality of longitudinal trenches may be formed by selectively removing the electrode material and dielectric material in the dielectric layer for forming of the trenches.

The longitudinal trenches between electrode areas may separate electrode material on adjacent ridges from each other, so that each electrode is defined by a coherent structure, possibly arranged on a plurality of ridges, wherein the electrode material on adjacent ridges within the electrode area is connected through connections interrupting the longitudinal trenches.

Thus, the structure of the device according to this embodiment may be formed by simple steps, also ensuring that the desired structure may be achieved with high yield.

The electrode material may be selectively removed, for instance by etching, from the stop areas. Alternatively, the electrode material may be selectively deposited, such that electrode material is not deposited in the stop areas.

According to an embodiment, the microelectrode array layer comprises separate areas of electrode material, each forming an individual electrode.

This implies that the electrode material is only arranged in the electrode area. Hence, there may be no or small risk of adjacent electrodes affecting each other as there may be a relatively large distance between electrode material of adjacent electrodes.

However, the arrangement of separate areas of electrode material may also require that electrode areas are formed by ensuring that electrode material is only present in selected, separate electrode areas.

According to an embodiment, the integrated circuit arrangement is configured for local amplification of signals acquired by the plurality of individual electrodes.

As mentioned above, thanks to the electrodes being arranged above the integrated circuit arrangement, the signals acquired by electrodes may be locally pre-processed. The signals may advantageously be locally amplified, which implies that a relatively small electrode area may be used while acquiring a signal of good quality, e.g. a high signal-to-noise ratio (SNR).

Thanks to the integrated circuit arrangement being arranged locally in relation to the electrodes, the integrated circuit arrangement may be configured to provide a differential amplifier so as to amplify a local electric potential across two adjacent electrodes. In this way, the sensing of electrical signals is less sensitive to external interference, as the signal is not sensed in relation to ground.

According to an embodiment, the device further comprises a plurality of pads extending through the dielectric layer for connecting the integrated circuit arrangement to external circuitry.

Thus, the signals acquired by the electrodes and locally processed by the integrated circuit arrangement may be read out to external circuitry for further processing of the signals and/or for analog-to-digital conversion of the signals and transferring the signals to an external processing unit, which may perform advanced analysis of the signal.

According to an embodiment, the electrodes are configured for reading out electrical signals from cells arranged on the surface of the device and/or for providing electrical stimulation to cells arranged on the surface of the device.

Thus, the electrodes may be used for reading out electrical signals from the cells. The electrodes may also be used for electrical stimulation of the cells in order to trigger a response from the cells which may be sensed or to provide small alternating currents to the cells for performing a bioimpedance measurement, such as impedance spectroscopy.

An electrode may be dynamically switched between providing electrical stimulation to cells and reading out electrical signals from cells.

Alternatively, some electrodes may be dedicated to reading out electrical signals, whereas other electrodes may be dedicated to providing electrical stimulation of the cells.

According to a second aspect, there is provided a method for manufacturing of a device for analysis of cells, said method comprising: forming a plurality of vias through a dielectric layer arranged above an integrated circuit arrangement on a substrate; forming a microelectrode array layer above the dielectric layer, wherein an individual electrode is associated with each of the plurality of vias; and forming a plurality of longitudinal trenches in the dielectric layer and the microelectrode array layer for stimulating cell growth on a surface of the device.

Effects and features of this second aspect are largely analogous to those described above in connection with the first aspect. Embodiments mentioned in relation to the first aspect are largely compatible with the second aspect.

Thanks to the method, electrodes may be formed in a microelectrode array layer and may be connected through vias in a dielectric layer to an integrated circuit arrangement allowing processing of signals acquired by the electrodes. Then, longitudinal trenches may be formed in the dielectric layer and the microelectrode array layer for stimulating cell growth. This implies that the manufactured device is especially suitable for culturing of cells on the device, while allowing acquiring of electrical signals from the cells by means of the electrodes of the microelectrode array layer.

According to an embodiment, said forming of the microelectrode array layer comprises depositing electrode material over an entire area of the microelectrode array layer except for limited stop areas between adjacent electrodes, said stop areas extending perpendicular to the longitudinal trenches, and wherein said forming of the plurality of longitudinal trenches isolates the individual electrodes from each other.

This implies that the microelectrode array layer may be easily formed without any need of forming complex or small structures in the microelectrode array layer. The longitudinal trenches between electrode areas may separate electrode material on adjacent ridges from each other, so as to isolate electrode areas from electrode material which is not to be part of the electrode area.

Thus, the structure of the device may be formed by simple steps, also ensuring that the desired structure may be achieved with high yield.

The deposition of the electrode material may be provided by any process that grows, coats or otherwise transfers a material onto a substrate, such as through physical vapor deposition (PVD), chemical vapor deposition (CVD), electrochemical deposition (ECD), molecular beam epitaxy (MBE) or atomic layer deposition (ALD).

According to an alternative embodiment, said forming of the microelectrode array layer comprises depositing electrode material in separate areas, each forming an individual electrode.

This implies that the electrode material is only deposited in areas which are to form electrode areas in the microelectrode array layer. Hence, there may be no or small risk of adjacent electrodes affecting each other as there may be a relatively large distance between electrode material of adjacent electrodes.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Figure 1:
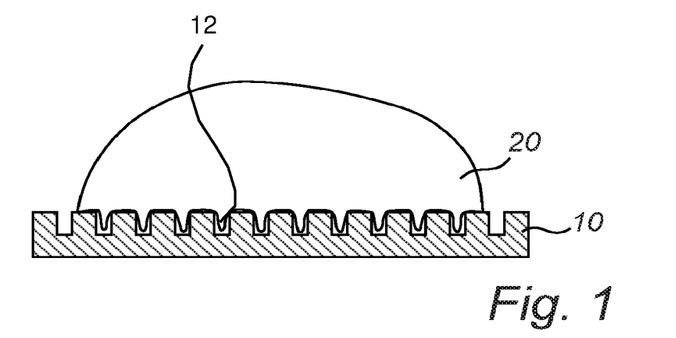
FIG. 1 is a schematic view illustrating cell growth on a surface.

FIG. 1 shows a cross-section of a surface 10 on which a cell 20 is cultured. The surface 10 is provided with grooves 12, which extend in a longitudinal direction on the surface 10. The grooves 12 may act to stimulate an organized directional growth of cells 20 on the surface 10. This implies that the cells 20 may grow in a similar manner on the artificial surface 10 as the cells 20 would grow in vivo.

For instance, a surface 10 with grooves 12 may be useful in culturing muscle cells or neuronal cells on an artificial surface 10. The culturing of cells 20 may be used for analyzing cell behavior. In this regard, it would be desired to acquire electrical signals from the cells 20.

Figure 2:
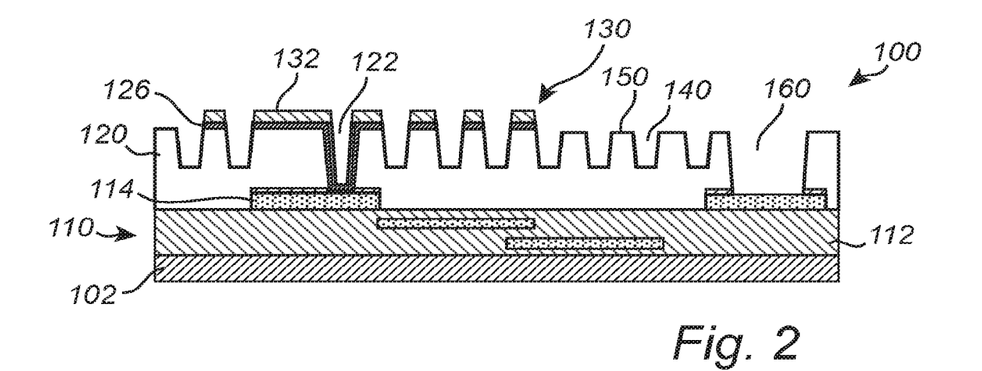
FIG. 2 is a schematic view illustrating a cross-section of a device for analysis of cells according to an embodiment.

Referring now to FIG. 2, a cross-section of a device 100 for analysis of cells 20 is shown. The device 100 enables acquiring of electrical signals from cells and/or providing of electrical signals to cells (e.g. for stimulating cells) in order to analyze cells growing on a surface of the device 100.

The device 100 comprises an integrated circuit arrangement 110 being provided on a substrate 102. The integrated circuit arrangement 110 may include components (transistors, resistors, capacitors, etc.) that may be formed on the substrate 102 in a miniaturized scale. The components may be arranged in order to provide functionality for processing acquired signals, which functionality may also be dynamically controlled by control signals.

As schematically illustrated in FIG. 2, the integrated circuit arrangement 110 may comprise back end of line (BEOL) layers 112 forming connections to the components on the substrate 102. The BEOL layers 112 may comprise a plurality of dielectric layers and conducting (metal) layers, wherein the metal layers are interconnected through vias in the dielectric layers.

A top metal layer 114 may form an interface for connecting to the components of the integrated circuit arrangement 110. The device 100 further comprises a dielectric layer 120 formed on the top metal layer 114 of the BEOL layers 112. A via 122 may be formed in the dielectric layer 120 in order to enable electrical connection to the top metal layer 114 through the dielectric layer 120.

The device 100 may further comprise a microelectrode array layer 130, which may be formed on the dielectric layer 120. Possibly, an intermediate layer 126 may be provided between the dielectric layer 120 and the microelectrode array layer 130, e.g. for improving attachment of the microelectrode array layer 130 on the dielectric layer 120.

The microelectrode array layer 130 may be patterned in order to define a plurality of electrodes 132 on the surface of the device 100. The plurality of electrodes 132 may define an array of electrodes 132 arranged in columns and rows for enabling contact with cells in a large number of discrete positions evenly distributed on the surface.

Each electrode 132 may be connected to the top metal layer 114 through the via 122 so as to enable transferring electrical signals between the cells and the integrated circuit arrangement 110.

The device 100 may further comprise a plurality of longitudinal trenches 140 in the dielectric layer 120 and the microelectrode array layer 130. The longitudinal trenches 140 may act to stimulate cell growth on the surface of the device 100.

By forming of longitudinal trenches 140, electrode material of the microelectrode array layer 130 is arranged on ridges 150 between the longitudinal trenches 140. The electrode material on the ridges 150 may provide contact with cells growing on the surface. Further, connections may be formed between the electrode material on adjacent ridges 150 so as to form a coherent structure of electrode material on at least two ridges 150. This implies that a relatively large electrode area 134 may be defined.

The coherent structure of the electrode 132 may further be connected through the via 122 to the integrated circuit arrangement 110. For instance, the electrode area 134 may be formed around the via 122.

The longitudinal trenches 140 may be formed so as not to extend through an entire thickness of the dielectric layer 120. This implies that the dielectric layer 120 may electrically isolate the integrated circuit arrangement 110 from any components on the surface of the device 100, such as ensuring that undesired electric connection between signals e.g. in the cells to the integrated circuit arrangement 110 is avoided. Hence, only connections through the vias 122 for connecting electrodes 132 to the integrated circuit arrangement 110 is provided in the dielectric layer 120. Thus, the vias 122 will have a larger depth than the longitudinal trenches 140.

A depth of a longitudinal trench 140 may be approximately 1 μm, whereas a depth of a via 122 may be approximately 1.5 μm, so as to ensure isolation of components on the surface of the device 100 from the integrated circuit arrangement 110. Further, a width of the longitudinal trench 140 may be approximately 0.5 μm.

It should be realized that other sizes of the widths and depth of the longitudinal trenches 140 may be used. The widths and depth of the longitudinal trenches 140 may be selected in order to provide desired stimulation of cell growth and may differ depending on the type of cells that are to be grown on the surface. For instance, a depth of the longitudinal trenches 140 may be in a range of 0.2-20 μm. A width of the longitudinal trenches 140 may be in a range of 0.2-6 μm.

The vias 122 may have equal widths as the longitudinal trenches 140 so as to facilitate aligning the vias 122 with respective longitudinal trenches 140. However, it should be realized that if a narrow width of the longitudinal trenches 140 is used, it may not be possible to ensure that the via 122 extends through the entire thickness of the dielectric layer 120 and, hence, the widths of the vias 122 may be selected to be wider than the widths of the longitudinal trenches 140.

Further, the device 100 may be provided with different widths and/or thicknesses of longitudinal trenches 140 in different parts of the surface of the device 100. Hence, the device 100 may be configured to stimulate different types of cell growth in different parts of the surface.

The integrated circuit arrangement 110 may be configured to provide a local processing of signals acquired by the electrodes 132. Control signals may be provided to the integrated circuit arrangement 110 for controlling functionality of the local processing to be performed and controlling timing of the processing.

The integrated circuit arrangement 110 may comprise a logic circuit which is designed for providing the desired functionality.

For instance, the integrated circuit arrangement 110 may be configured to provide multiplexing of signals, such that signals from a plurality of electrodes 132 may be sequentially output by the integrated circuit arrangement 110 to an external circuitry.

Further, the integrated circuit arrangement 110 may be configured to amplify a signal from an electrode 132. Local amplification of the signal may be useful in ensuring that a size of an electrode 132 may be relatively small, while allowing an electrical signal in a cell to be properly sensed.

Also, the integrated circuit arrangement 110 may be configured to set a sensing modality of the electrode 132, such that different types of signals may be acquired, e.g. by setting a frequency of the signal to be acquired.

Further, the electrode 132 may be used both for acquiring a signal from a cell and for providing a stimulating signal to the cell. Thus, the integrated circuit arrangement 110 may be configured to switch for using the electrode 132 for acquiring a signal or for providing a stimulation signal.

It should also be realized that electrodes may alternatively be dedicated to either providing stimulation signals to the cells or for acquiring signals from the cells.

The integrated circuit arrangement 110 may further be configured in order to enable differential amplification. Thus, the integrated circuit arrangement 110 may be configured so as to measure a local electric potential across two electrodes. In this way, the acquiring of signals may be less sensitive to interference. The integrated circuit arrangement 110 may in such case also be configured for dynamically selecting an electrode to be used as a reference node in the differential amplification.

The device 100 may further comprise additional vias 160 in the dielectric layer 120 for enabling a plurality of pads to be connected to the top metal layer 114 of the BEOL layers 112 for forming a connection to the integrated circuit arrangement 110. The pads may be connected to wires enabling the device to be connected to external circuitry.

The pads may thus enable the integrated circuit arrangement 110 to be connected to external circuitry. The external circuitry may provide control signals to the integrated circuit arrangement for controlling functionality of the integrated circuit arrangement and/or may enable further processing of the signals acquired by the electrodes 132 and the integrated circuit arrangement 110. For instance, the external circuitry may enable analog-to-digital conversion of acquired signals, which may further facilitate transfer of acquired signals to a remote processing unit.

Figure 3:
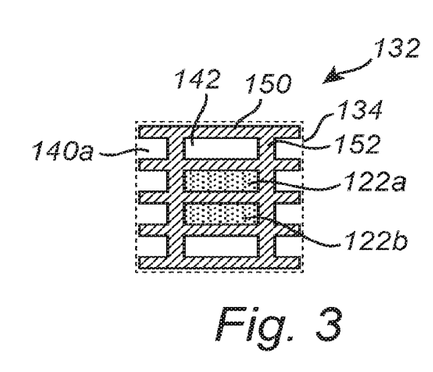
FIG. 3 is a top view of an electrode of the device according to a first embodiment.

Referring now to FIG. 3, a structure of an electrode 132 according to an embodiment will be further described. FIG. 3 is a top view of the electrode 132.

As shown in FIG. 3, electrode material may be provided on ridges 150. The electrode material on the ridges 150 may be connected by connecting parts 152, which extend in a direction perpendicular to the longitudinal trenches 140. The connected parts of electrode material may form a coherent structure that is confined to a rectangular area, forming an electrode area 134, as illustrated by dashed lines in FIG. 3. The electrode 132 may thus be in electric contact with a cell in the electrode area 134.

The electrode area 134 may be formed so as to avoid interrupting of the longitudinal trenches 140 such that the arrangement of electrodes 132 on the surface of the device 100 should not affect the desired cell growth on the surface.

Thus, grooves 142 may be formed in the electrode area 134, wherein the grooves 142 extend in a common direction along a common straight line and are thus aligned with respective longitudinal trenches 140 so as to contribute to stimulating of cell growth on the surface. Further, a longitudinal trench 140a may extend into the electrode area 134 in order to ensure that a large, uninterrupted distance of the longitudinal trench 140a may be arranged on the surface.

In FIG. 3, the electrode 132 is illustrated having two connecting parts 152 extending between ridges 150. However, it should be realized that only a single connecting part 152 may be provided. In such case, the connecting part 152 may be arranged to connect to a central portion of the electrode material on the ridges 150. This implies that no groove 142 may be needed in the electrode area 134. Instead, the longitudinal trenches 140 on opposite sides of the connecting part 152 may extend far into the electrode area 134.

It should also be realized that more than two connecting parts 152 may be provided between the ridges 150, with a plurality of grooves 142, each groove 142 being arranged between pairs of connecting parts 152.

Further, in the embodiment illustrated in FIG. 3, the electrode 132 is connected through two vias 122a, 122b to the integrated circuit arrangement 110. The use of two vias 122a, 122b connecting the electrode 132 to the integrated circuit arrangement 110 may ensure a higher yield in manufacturing of devices, as a redundancy in connection between the electrode 132 and the integrated circuit arrangement 110 is introduced.

However, it should be realized that a single via 122 may be used instead, or that more than two vias 122a, 122b may be used.

As illustrated in FIG. 3, the one or more vias 122 may be aligned with respective longitudinal trenches 140 so as to contribute to stimulating of cell growth on the surface.

The microelectrode array layer 130 may be patterned to form a plurality of distinct electrode areas 134. The electrode material may thus be deposited in each electrode area 134 and then the longitudinal trenches 140 and, possibly grooves 142, may be formed, e.g. by selective etching, in order to form the structure of each electrode 132 as illustrated in FIG. 3.

Figure 4:
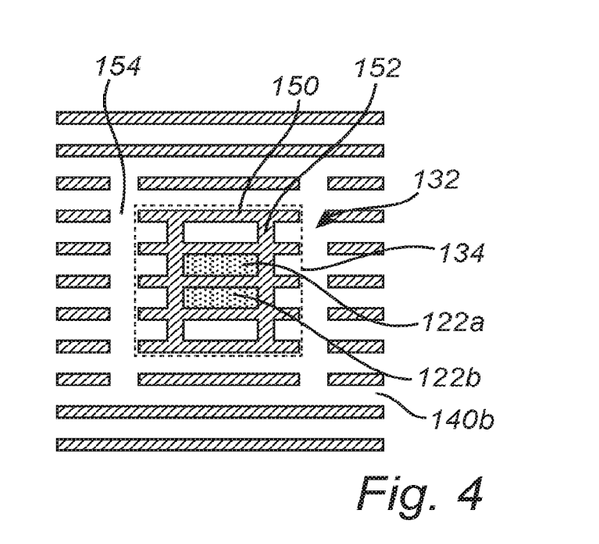
FIG. 4 is a top view of an electrode of the device according to a second embodiment.

Referring now to FIG. 4, a structure of an electrode 132 according to another embodiment will be further described. FIG. 4 is a top view of the electrode 132 and an area around the electrode area 134.

The structure illustrated in FIG. 4 may be formed by means of depositing electrode material in an entire area of the microelectrode array layer 120, except for stop areas 154, which are defined by lines extending in a perpendicular direction of the longitudinal trenches 140 (to be formed), wherein a stop area 154 is arranged between each pair of adjacent electrodes 132, such that two stop areas 154 will be arranged on opposite sides of the electrode 132 (as illustrated in FIG. 4).

The stop area 154 may be shared by two adjacent electrodes 132. However, according to an alternative, each electrode 132 is associated with its own two stop areas 154.

When the longitudinal trenches 140 are formed, the electrode 132 may be defined by the longitudinal trenches 140 isolating the electrode material in the electrode area 134 from other electrode material. As illustrated in FIG. 4, electrode material will remain on ridges 150, without being connected to any electrode 132 and, hence, not affecting acquiring of signals with the electrodes 132 that are connected to the integrated circuit arrangement 110.

As shown in FIG. 4, the electrode 132 formed based on deposition of electrode material in substantially the entire microelectrode array layer 130 (except for the stop areas 154) may have a similar structure as the electrode 132 shown in FIG. 3, which is formed by deposition of electrode material in distinct electrode areas 134.

It should be realized that many alternative designs of a shape of the electrodes 132 could be used. For instance, a size of the electrode 132 may differ or the number of grooves 142 or patterns within the electrode area 134 may differ.

Figure 5:
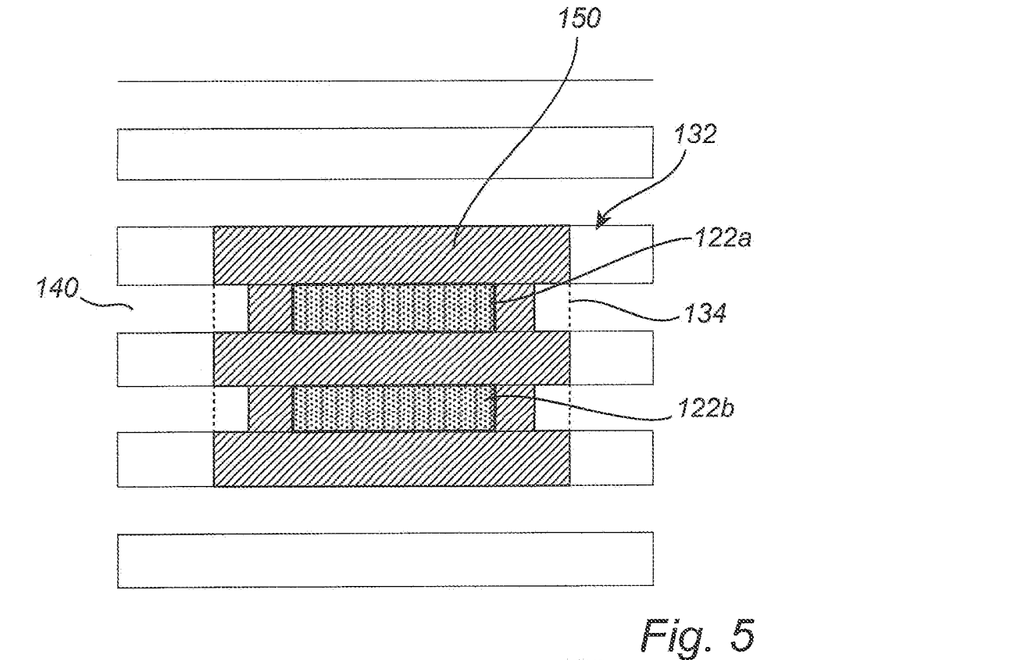
FIGS. 5-6 are top views of alternative patterns of the electrode of the device.
Figure 6:
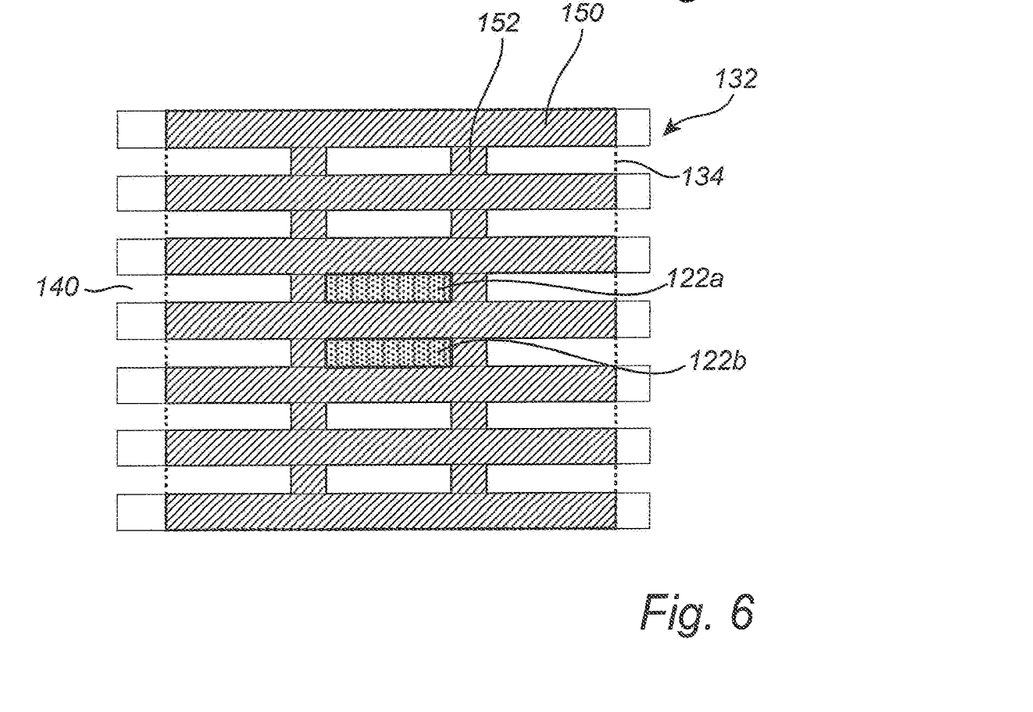

Referring now to FIGS. 5-6, two different embodiments of electrodes 132 are shown, which may be used with deposition of the electrode material in distinct area as discussed in relation to FIG. 3 or with deposition of electrode material in the "entire" microelectrode array layer 130 as discussed in relation to FIG. 4.

In FIG. 5, the electrode 132 is illustrated being formed around two vias 122a, 122b, which are aligned with longitudinal trenches 140. The electrode area 134 is limited to three ridges 150, which are arranged on opposite sides of the vias 122a, 122b and between the vias 122a, 122b. Thus, no groove is formed in the electrode area 134.

In FIG. 6, the electrode 132 is illustrated being formed on a plurality of ridges 150 (seven ridges). The vias 122a, 122b are formed in a central part of the electrode area 134. A plurality of grooves 142 are formed in the electrode area 134.

The vias 122a, 122b of the electrode 132 in FIG. 6 has a similar size as the vias 122a, 122b illustrated in FIG. 5. Connecting parts 152 are arranged on opposite sides of the vias 122a, 122b in tight relation thereto.

Further, the electrode 132 is illustrated to have a quadratic shape. This implies that the longitudinal trenches 140 extend farther into the electrode area 134 to the connecting parts 152 compared to the longitudinal trenches extending into the electrode area 134 in FIG. 5.

Referring now to FIGS. 7-14, a method for manufacturing of the device 100 will be further described.

An integrated circuit arrangement 110 may be formed on a substrate 102 and may be designed in view of desired functionality. Further, BEOL layers 112 may be formed on the components of the integrated circuit arrangement 110 in order to provide interconnections between the components. A top metal layer 114 may be provided in the BEOL layers 112 to provide availability for forming connections to the integrated circuit arrangement 110.

The integrated circuit arrangement 110 may be formed by semiconductor manufacturing as known to a person skilled in the art. The device 100 may further be manufactured by forming layers above the integrated circuit arrangement 110 as will be described in further detail below. The forming of layers on the top metal layer 114 may be performed in BEOL processing, immediately after the top metal layer 114 has been formed.

Figure 7:
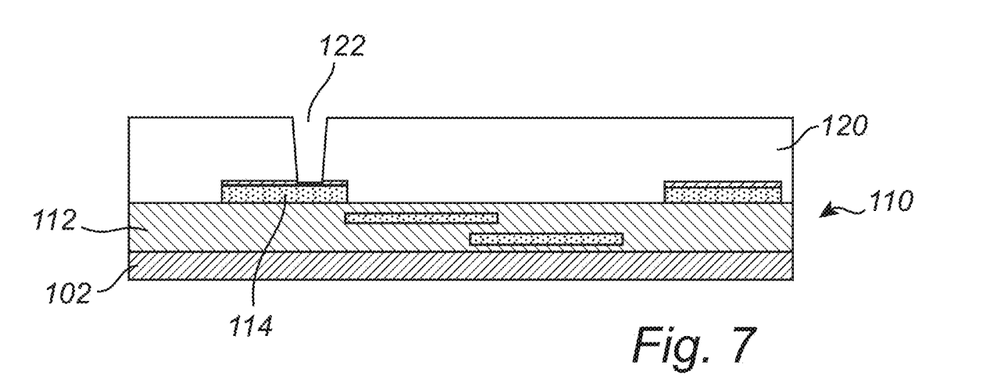
FIGS. 7, 9, and 12 are cross-sections illustrating different steps in manufacturing of the device.

As illustrated in FIG. 7, a dielectric layer 120 may be deposited on the top metal layer 114 and may be planarized. The dielectric layer 120 may be formed by $SiO_2$, but it should be realized that any dielectric material may be used in order to isolate the integrated circuit arrangement 110 from components above. The dielectric material may be selected from a material that may be appropriately used in BEOL processing.

Figure 8:
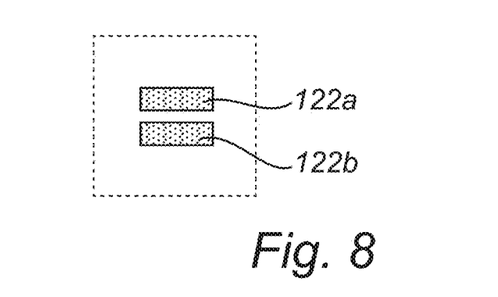
FIGS. 8, 10, 11, 13 and 14 are top views illustrating masks used in manufacturing of the device.

Then, vias 122 for each electrode 130 are formed in the dielectric layer 120 to extend to the top metal layer 114. A mask as illustrated in FIG. 8 may be used in selective removing, e.g. by etching, of the dielectric material of the dielectric layer 120 for forming vias 122a, 122b. The mask of FIG. 8 illustrates the pattern to be formed for one electrode 132. It should be realized that this pattern may be repeated so as to simultaneously form a plurality of vias for a plurality of electrodes 132.

Figure 9:
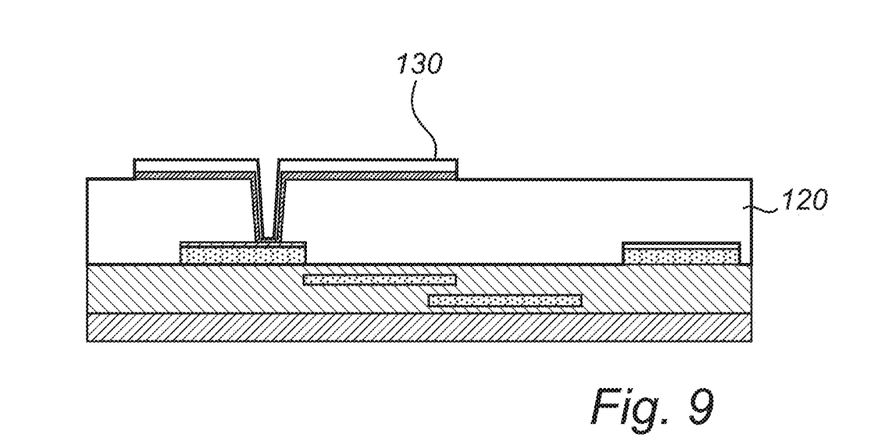

Next, as illustrated in FIG. 9, a microelectrode array layer 130 is deposited. This may be performed in two steps, as an intermediate layer for improving attachment of the microelectrode array layer 130 may first be deposited on the dielectric layer 120.

The microelectrode array layer 130 may be formed by TiN, but it should be realized that any conducting material may be used in order to provide electrodes 132 that may acquire electrical signals from cells. The material of the microelectrode array layer 130 may be selected from a material that is electrically conducting and may be appropriately used in BEOL processing.

The microelectrode array layer 130 may be formed by selective deposition using a mask, or by a first deposition step followed by selective etching of the microelectrode array layer 130.

Figure 10:
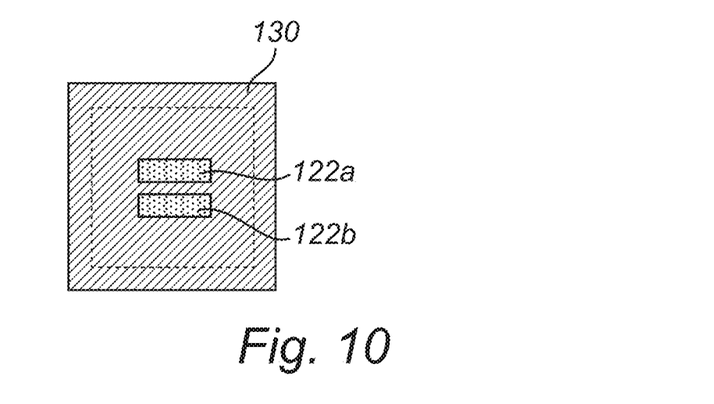

According to one embodiment, the microelectrode array layer 130 may form discrete areas of electrode material. In FIG. 10, a mask to be used in this embodiment is illustrated.

Figure 11:
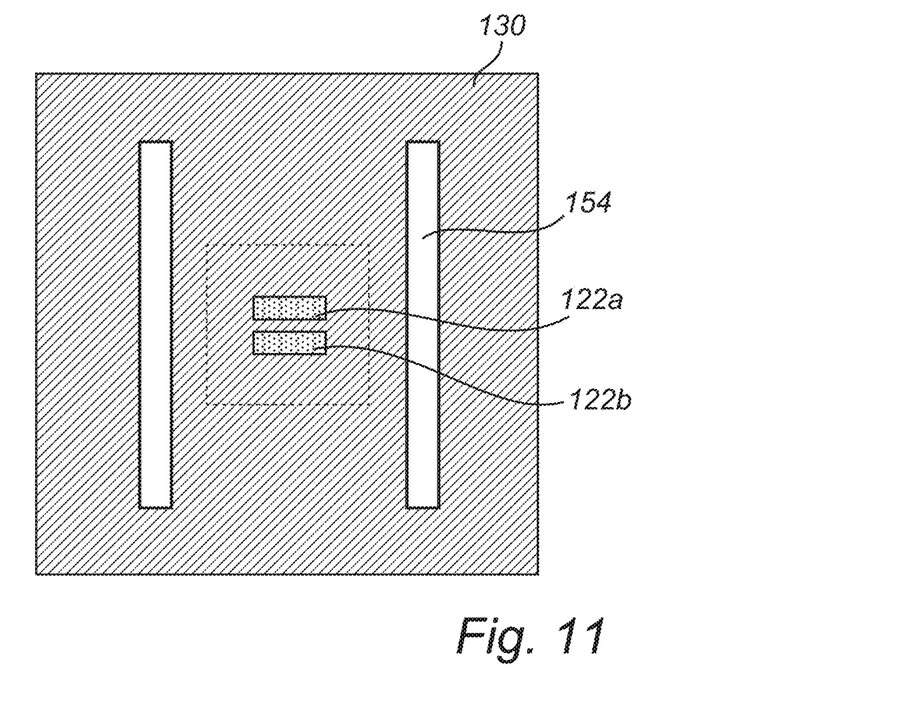

According to another embodiment, the microelectrode array layer 130 is arranged generally on the dielectric layer. In FIG. 11, a mask to be used in this embodiment is illustrated.

As shown in FIG. 10, the electrode material for an electrode 132 is selectively deposited in the electrode area 134 to be formed. A square shape corresponding to the electrode area 134 may be defined by the mask and electrode material may be deposited only in electrode areas 134.

Although only a mask corresponding to one electrode 132 is illustrated in FIG. 11, the electrode material may be deposited in the entire microelectrode array layer 130 such that the electrode material deposited with the mask illustrated in FIG. 11 may be integral between adjacent electrodes 132. As illustrated in FIG. 11, stop areas 154 may be formed on opposite sides of an electrode area 134 to be formed.

Figure 12:
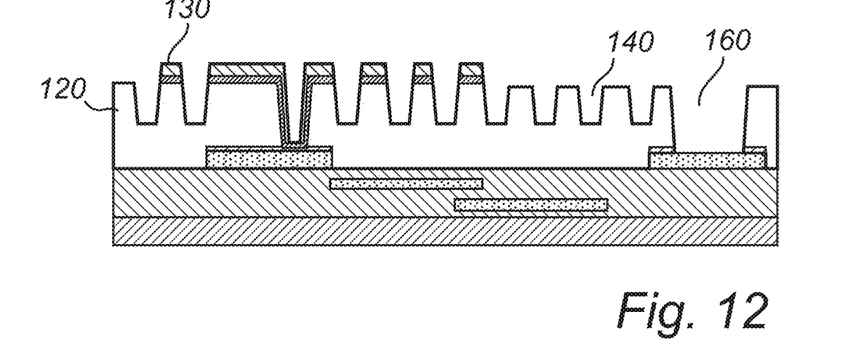

Finally, as illustrated in FIG. 12, longitudinal trenches 140 may be formed. The longitudinal trenches 140 may be formed by selective etching of electrode material of the microelectrode array layer 130 and dielectric material of the dielectric layer 120 so as to form parallel trenches extending in a longitudinal direction on the surface of the device 100.

Figure 13:
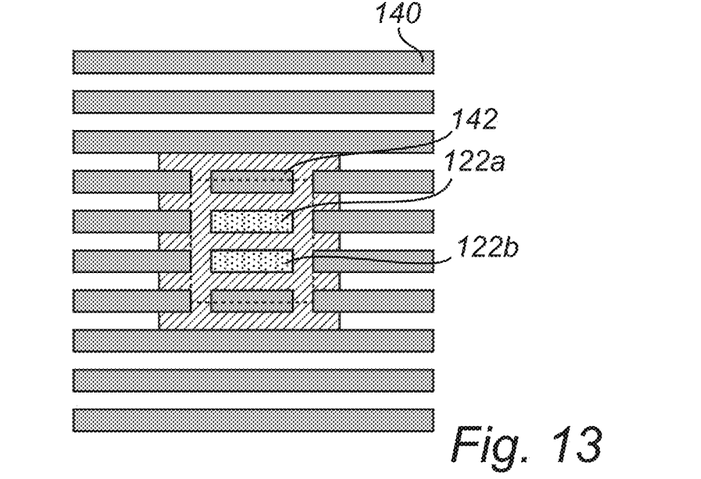
Figure 14:
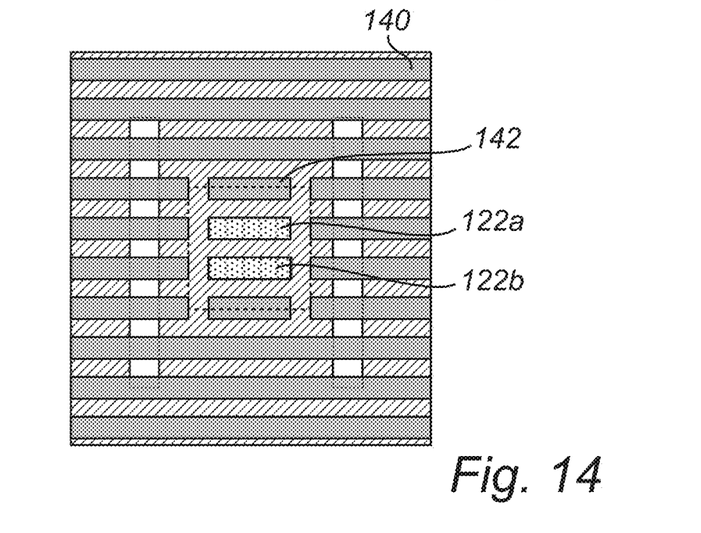

The longitudinal trenches 140 may be formed using a mask as illustrated in FIGS. 13-14, in relation to the embodiments of masks in FIGS. 10 and 11, respectively. The etching of longitudinal trenches 140 may be provided in areas marked in gray in the masks of FIGS. 13-14. As is clear from FIGS. 13-14, the same mask may be used in both embodiments.

However, for the embodiment illustrated in FIG. 14, the etching of longitudinal trenches 140 implies that ridges 150 between the trenches 140 will be covered by electrode material.

Some longitudinal trenches 140a may extend partially into the electrode area 134. Other longitudinal trenches 140b (see FIG. 4) may not intersect the electrode area 134 and may hence extend uninterrupted past a plurality of electrode areas 134 or even over an entire area of the microelectrode array layer 130.

Simultaneously with the forming of longitudinal trenches 140, the grooves 142 in electrode areas 134 may also be formed. Further, as illustrated in FIG. 12, additional vias 160 for enabling a pad to connect to the integrated circuit arrangement 110 may also be formed.

It should be realized that the integrated circuit arrangement 110 may be provided with a dielectric material 120 in order to isolate and protect the integrated circuit arrangement 110. The thus manufactured device may be shipped to another manufacturing party for forming the microelectrode array layer 130 and the longitudinal trenches 140 of the device 100.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For instance, electrode areas 134 have been mainly described in relation to rectangular or square shapes. However, it should be realized that other shapes of the electrode areas could equally well be used, such as forming of circular areas.

The invention claimed is:

1. A device for analysis of cells, said device comprising:
    an integrated circuit arrangement on a substrate;
    a dielectric layer formed above the integrated circuit arrangement;
    a microelectrode array layer formed above the dielectric layer, said microelectrode array layer comprising a plurality of individual electrodes formed of electrode material, wherein each electrode is connected to the integrated circuit arrangement through a via in the dielectric layer; and wherein a plurality of longitudinal trenches in the dielectric layer and the microelectrode array layer are for stimulating cell growth on a surface of the device,
    wherein the plurality of longitudinal trenches are spaced by a plurality of ridges,
    wherein each longitudinal trench of the plurality of longitudinal trenches is defined between adjacent spaced ridges of the plurality of ridges that form a top-most surface of the dielectric layer, and
    wherein each longitudinal trench has walls extending longitudinally in a direction from the adjacent spaced ridges towards a bottom-most surface of the dielectric layer to a longitudinal trench bottom,
    wherein the microelectrode array layer is arranged as electrode material disposed only on the ridges, and
    wherein electrode material in an individual electrode on adjacent ridges is electrically connected across the longitudinal trenches by a connecting member extending in a direction perpendicular to the longitudinal trenches, and
    wherein each individual electrode in the microelectrode array layer forms an electrode area and the electrode material in the electrode area forms a coherent structure.

2. The device according to claim 1, wherein each via for connecting each individual electrode to the integrated circuit arrangement are formed in each electrode area.

3. The device according to claim 2, wherein two vias for connecting each individual electrode to the integrated circuit arrangement are formed in each electrode area.

4. The device according to claim 1, wherein the plurality of longitudinal trenches are arranged to extend into each electrode area.

5. The device according to claim 1, wherein a groove extending in a common direction with a longitudinal trench of the plurality of longitudinal trenches is arranged within each electrode area.

6. The device according to claim 1, wherein a longitudinal trench of the plurality of longitudinal trenches extends across an entire area of the microelectrode array layer.

7. The device according to claim 1, wherein the device further comprises stop areas extending perpendicular to the longitudinal trenches, wherein no electrode material is arranged in the stop areas so as to isolate individual electrodes from each other.

8. The device according to claim 1, wherein the microelectrode array layer comprises separate areas of electrode material, each forming an individual electrode.

9. The device according to claim 1, wherein the integrated circuit arrangement is configured for local amplification of signals acquired by the plurality of individual electrodes.

10. The device according to claim 1, further comprising a plurality of pads extending through the dielectric layer for connecting the integrated circuit arrangement to external circuitry.

11. The device according to claim 1, wherein the electrodes are configured for reading out electrical signals from cells arranged on the surface of the device and/or for providing electrical stimulation to cells arranged on the surface of the device.

12. A method for manufacturing of a device for analysis of cells, said method comprising:
    forming a plurality of vias through a dielectric layer arranged above an integrated circuit arrangement on a substrate;
    forming a microelectrode array layer above the dielectric layer, said microelectrode array layer comprising a plurality of individual electrodes formed of electrode material, wherein each electrode is connected to the integrated circuit arrangement through a via in the dielectric layer;
    forming a plurality of longitudinal trenches in the dielectric layer and the microelectrode array layer for stimulating cell growth on a surface of the device,
        wherein the plurality of longitudinal trenches are spaced by a plurality of ridges,
        wherein each longitudinal trench of the plurality of longitudinal trenches is defined between adjacent spaced ridges of the plurality of ridges that form a top-most surface of the dielectric layer, wherein each longitudinal trench has walls extending longitudinally in a direction from the adjacent spaced ridges towards a bottom-most surface of the dielectric layer to a longitudinal trench bottom; and wherein the microelectrode array layer is arranged as electrode material disposed only on the ridges; and electrically connecting electrode material in an individual electrode on adjacent ridges across the longitudinal trenches by a connecting member extending in a direction perpendicular to the longitudinal trenches, wherein each individual electrode in the microelectrode array layer forms an electrode area and the electrode material in the electrode area forms a coherent structure.

13. The method according to claim 12, wherein said forming of the microelectrode array layer comprises depositing the electrode material over an entire area of the microelectrode array layer except for stop areas between adjacent electrodes, said stop areas extending perpendicular to the longitudinal trenches, and wherein said forming of the plurality of longitudinal trenches isolates the individual electrodes from each other.

14. The method according to claim 12, wherein said forming of the microelectrode array layer comprises depositing the electrode material in separate areas, each forming an individual electrode.

15. The device according to claim 1, wherein the microelectrode array layer is discontinuous between adjacent longitudinal trenches of the plurality of longitudinal trenches.

* * * * *